United States Patent [19]

Ness

[11] 4,058,125

[45] Nov. 15, 1977

[54] FORCE DISTRIBUTING ADHESIVE TAPE TAB FOR DISPOSABLE DIAPERS

[75] Inventor: Irving S. Ness, Princeton, N.J.

[73] Assignee: Johnson & Johnson, New Brunswick, N.J.

[21] Appl. No.: 699,013

[22] Filed: June 23, 1976

Related U.S. Application Data

[63] Continuation-in-part of Ser. No. 659,313, Feb. 19, 1976.

[51] Int. Cl.$^2$ ............................................. A61F 13/16
[52] U.S. Cl. ..................................... 128/287; 128/284
[58] Field of Search ....................... 128/287, 284, 156; 24/DIG. 11, 67

[56] References Cited

U.S. PATENT DOCUMENTS

| | | | |
|---|---|---|---|
| 2,740,403 | 4/1956 | Schueler | 128/156 |
| 3,810,472 | 5/1974 | Aldinger et al. | 128/287 |
| 3,811,438 | 5/1974 | Economou | 128/156 |
| 3,853,129 | 12/1974 | Kozak | 128/287 |
| 3,870,041 | 3/1975 | Davies | 128/156 |
| 3,967,624 | 7/1976 | Milnamow | 128/284 X |

*Primary Examiner*—Stephen C. Pellegrino

[57] ABSTRACT

An improved adhesive tape tab for use on disposable diapers which distributes fastening and peeling forces to both the inside and outside surfaces thereof, thereby reducing stress levels on any one surface of the diaper. The tape tab has a tape which has a first portion fastened on one surface of the diaper. A second, extendable portion of the tape has adhesive material thereon. A flexible, open-mesh sheet material has a first portion attached to the adhesive surface on the second portion of the tape; a second portion of the sheet material is attached to the surface of the diaper opposite from the surface which the first portion of the tape is attached. By this "Y" structure arrangement, during use of the diaper fastening or peeling forces transmitted by the second portion of the tape are distributed to both surfaces of the diaper.

8 Claims, 4 Drawing Figures

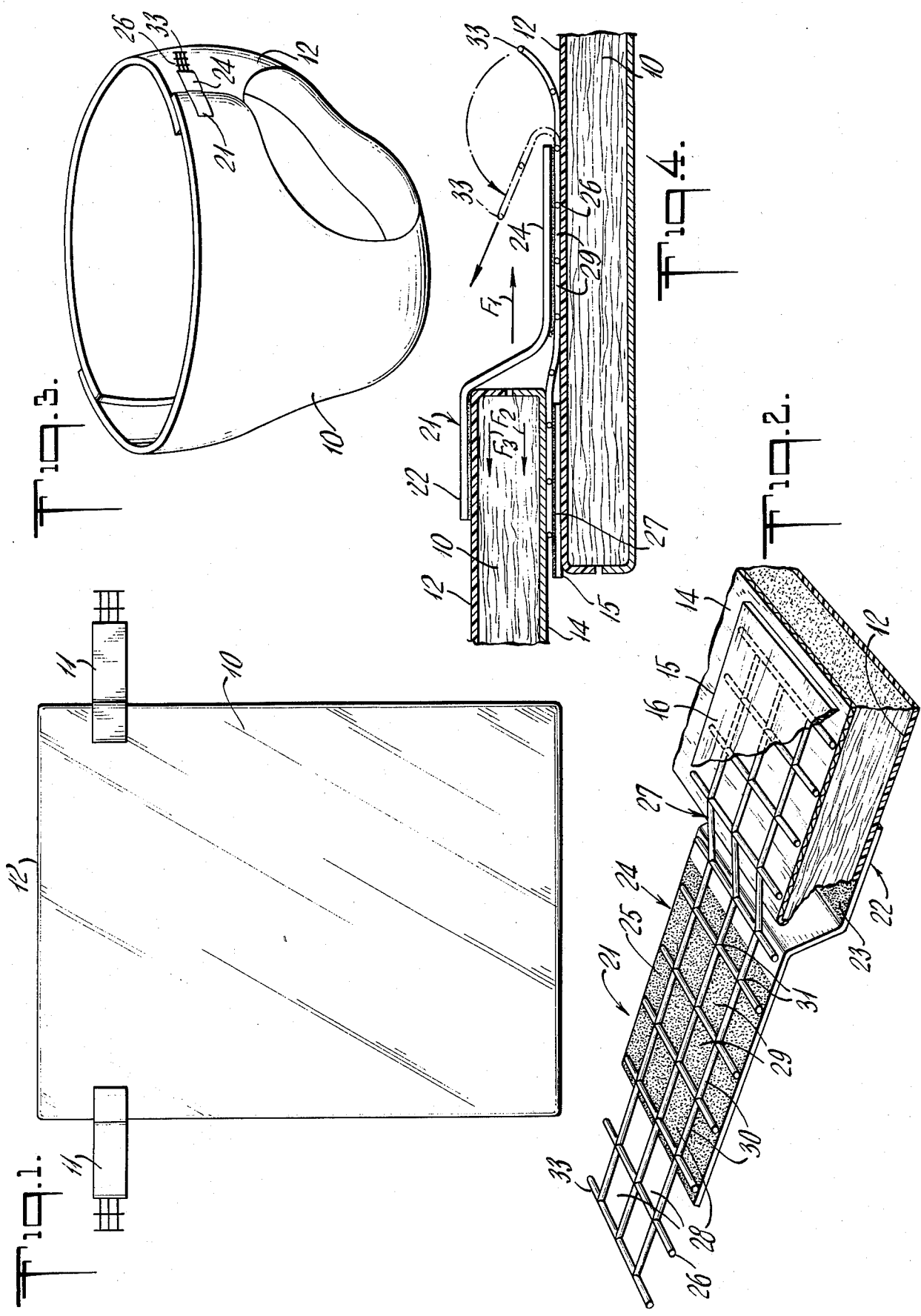

FORCE DISTRIBUTING ADHESIVE TAPE TAB FOR DISPOSABLE DIAPERS

This application is a continuation-in-part of application Ser. No. 659,313, filed Feb. 19, 1976.

BACKGROUND OF THE INVENTION

This invention relates to an improved adhesive tape tab for use on disposable diapers. More particularly, this invention relates to an improved adhesive tape tab which permits fastening forces on the tape to be distributed to both sides of a disposable diaper during use, and to certain embodiments of the diaper which are to be opened after a closure has been made without tearing the outside film of the diaper or the tape tab itself, and which can be repositioned and re-used for subsequent fastenings of the diaper.

It has become very common and practical to use adhesive tape tabs on disposable diapers. The practicality of tape tabs, rather than pins, is self-evident. One of the problems which has occurred, however, when using adhesive tape tabs is tearing of the outside film to which it is attached. When one part of the tape is secured to the plastic film and the other part is fastened to another part of the diaper during use, the stresses are often too great thereby causing the plastic film to tear. A technique to overcome this problem has been proposed in U.S. Pat. No. 3,848,594, whereby the stresses are transmitted to both the front and back surfaces of the diaper. However, there are limitations in the functional uses and versatility of the technique in the mentioned patent. As will be described hereinafter, versatility of the tape tab of the present invention offers specific advantages over the presently known tape tabs which distribute forces to both sides of the diaper.

There are also shortcomings in the use of adhesive tape tabs which become evident especially when the diaper needs checking for soiling or for repositioning. For instance, when a child reaches the stage of toilet training the diaper must be opened and removed, and if not soiled, could be used again. The prime or major shortcoming in the known adhesive tape tabs is the lack of easy separability from the diaper once the original closure has been made. To separate the adhesive tape tab from the surface of the diaper on most, if not all, occasions either the outside surface of the diaper, usually a thin, plastic film, is torn or the tape tab itself is torn. A torn tape tab or a torn diaper outside surface makes refastening very cumbersome if not, practically, impossible. Furthermore, the consumer has had to discard unsoiled diapers because the attempt to open the diaper has torn the outside of the diaper too much to make a subsequent closure. This lack of re-use is an economic disadvantage and an expensive burden due to the cost of disposable diapers.

The above tearing problems arise from use of a very thin plastic film as the outside surface on nearly all disposable diapers. This plastic film, being thin, is economical, flexible, somewhat supple, and most importantly, is impermeable so as to act as a fluid barrier for retaining fluids within the diaper. While the known adhesive tape tabs make a good, strong fastening on this film when the diaper is in use, the thin nature of the film allows the film to easily tear when fastening forces are too great or attempts are made to peel the tapes from the film. Of course, making the plastic films somewhat thicker is a possible means of increasing the strength of the film. However, the cost of the thicker film is increased, its flexibility and suppleness reduced, while no assurance is gained that tearing will not occur under variable tape fastening conditions.

Recently, there have been attempts to provide disposable diapers with adhesive tape tabs which can be used more than once. In U.S. Pat. No. 3,848,596, the tape tab fastening means provides an arrangement which is essentially useful for only two fastenings, the original and one more. Use of multiple release sheets on the tape tabs provides the refastening ability. The multiple release sheets are, however, limiting elements in the refastening or repositioning ability of the tapes, and add cost in the manufacture of the diapers. Besides the cost factor, the use of multiple release sheets does not overcome the problem of tearing either the outside of the diaper or the tape tab itself in order to open the diaper after the original closure has been made. In those instances when the outside diaper film is torn, the absorbent material inside the diaper is exposed, may drop out of the diaper in pieces and does not permit any neat and effective refastening of the diaper around the wearer. Consequently, the diaper has to be discard, even though it may not be soiled.

The tape fastener disclosed in U.S. Pat. No. 3,853,129 is so constructed as to be used on disposable diapers without the need of a release paper. The tape fastener has a middle segment having a plastic material with a retiform surface; the tape is folded when the diaper is in the non-operating position so that a releasable adhesive end surface of the tape lies against the surface of the plastic material. The middle plastic segment and the shape of the fold allows the tape tab to be used without a release paper. In use, however, this tape tab with the retiform plastic material creates additional holding power against the backing sheet of the diaper and cannot be separated after closure without, on most occasions, tearing the diaper backing sheet or tearing the tab itself.

SUMMARY OF THE INVENTION

An improved, economical adhesive tape tab for use on a disposable diaper of the type having an inside surface and an outside surface now overcomes the deficiencies of diaper tape tabs, as listed above, as well as providing advantages of its own. As a primary advantage the improved tape tab allows the fastening forces on the adhesive tape to be distributed to both sides of the diaper, especially when initially wrapping the diaper around the wearer, thereby reducing the levels of stress which are exerted on the thin plastic film causing the film to tear. In addition, the structure of the improved tape tab provides greater functionality and versatility when used on disposable diapers. Specifically, this improved tape tab can be used for opening and refastening disposable diapers on many occasions throughout the service of the diaper.

A prominent advantage of this new adhesive tape tab is the cost savings gained from using disposable diapers many times or until soiled. Especially in circumstances where the diaper has need to be opened, such as with children in the toilet-training stage, is the re-usability feature a significant advantage. In this respect one diaper may be opened and removed from the child in toilet training and re-used if not soiled. Previously, a new diaper would have had to be used since the known diaper tape tabs do not accommodate the re-usability feature. Besides a cost savings, the re-use of the same diaper is a convenience measure since an additional diaper does not have to be available every time the child makes an attempt to learn the significance of the toilet.

In addition to the features mentioned above, the preferred and other embodiments of this new adhesive tape tab may be utilized on the disposable diaper without the need of a separate protective release sheet. Elimination of release sheets on disposable diapers overcomes the discardal problems associated with entirely removable protective release sheets while effecting a cost savings by not having to use any type of protective covering on the adhesive tape tab.

In accordance with the principles of this invention an improved adhesive tape tab is provided for disposable diapers having an inside surface and an outside surface. The tape tab of the present invention has a tape with a first portion attached to one surface of the diaper and a second, extendable portion for attachment to another part of the diaper. On one surface of at least the second portion of the tape there is an adhesive material. A flexible, open-mesh sheet material has a first portion thereof attached to the adhesive surface of the second portion of the tape. A second portion of the sheet material is attached to the surface of the diaper opposite from the surface which the first portion of the tape is attached. This arrangement permits fastening forces transmitted by the second extendable portion of the tape to be distributed to the inside and outside surfaces of the diaper.

In the preferred and other embodiments of this invention the outside surface of the diaper is generally a thin, plastic film and the second, extendable portion of the tape is fastened to this film during use. The first portion of the open-mesh sheet material covers substantially the entire second, extendable portion of the tape; the sheet material is comprised of filaments and intersections, forming openings, or segments, of a thin, flexible plastic open-mesh netting. Each segment or opening has an area so that the peel strength between the second portion of tape and the film over the segmented area is less than the tearing strength of the film over the same segmented area. When the second portion of the tape is peeled from the film over these distinct, smaller adhesive segments, the tearing strength of the plastic film is not exceeded as it would be over the entire adhesive surface without being divided. As a convenient pull-tab for peeling the tape tab from the diaper this embodiment includes a segment of the plastic netting extending beyond the furthest or distal edge of the tape.

The structure of this new adhesive tape tab permits a sealed tape to be separated from the thin, plastic film of the diaper without any tearing. Uniform distribution of peeling forces and reduced tear stress area over which the tape is peeled, provided by the segmented adhesive areas, permit a surprisingly convenient separation between tape and diaper. Such ready separability and good, strong closures upon subsequent fastenings provide the economical and practical advantages of this embodiment of the present invention.

BRIEF DESCRIPTION OF THE DRAWINGS

These and other advantages, features and aspects of the invention will become apparent upon reading the following detailed description and upon reference to the accompanying drawings wherein:

FIG. 1 is a plan view of a typical disposable diaper, showing the new tape tab attached;

FIG. 2 is a bottom perspective view showing the preferred embodiment of the improved tap tab;

FIG. 3 is a perspective view showing the diaper in a fastened condition secured with the improved adhesive tape tab; and FIG. 4 is a cross-sectional view of the fastened diaper depicting the transmittal of fastening forces and their distribution While the invention will be described in connection with a preferred embodiment, it will be understood that it is not intended to limit the invention to that embodiment. On the contrary, it is intended to cover all alternatives, modifications and equivalents as may be included within the spirit and scope of the described invention.

DETAILED DESCRIPTION OF THE DRAWINGS

With particular reference to FIG. 1, there is shown a disposable type diaper 10 with an improved adhesive tape tab 11 attached at two places to a part of the diaper. In this instance the tabs are shown attached to the outside surface 12 of the diaper; depending upon the fold of the diaper along the sides, however, the tabs may be attached to the inside surface or at some position between the inside and outside surfaces, whatever is practicable.

A bottom perspective view in FIG. 2 shows the detailed structure of the preferred embodiment of the improved adhesive tape tab. A tape 21 has a first portion 22 fastened to the outside surface 12 of the diaper. This outside surface 12 is a thin, plastic film, generally in the range of 0.00075–0.0015 inch (0.0019–0.0038 cm.) thick. Typical materials used on the outside plastic film include polypropylene, polyethylene, and the like. The first portion 22 may have an adhesive layer 23 on one surface in order to be fastened to the diaper as seen in the drawings; or, the part of the diaper to which the tape is to be attached may be adhesively treated to provide the fastening capabilities. The attachment of the tape tab to the diaper may be accomplished by any means seen fit to be employed.

Extending from the first portion of tape is a second extendable portion 24. On one surface of the second portion of tape is an adhesive material 25. While the adhesive may cover substantially the entire surface of the second portion, preferably there is no adhesive material in an area immediately adjacent the edge of the diaper as seen in FIG. 2. This lack of adhesive in this area prohibits the tape from sticking to the edge of the diaper where any adhesive attachment may induce tearing of the film at that edge. This extendable, second portion 24 of tape with the adhesive material 25 thereon is intended to be used to fasten the diaper around the wearer. The second portion 24 is fastened to another part of the diaper by being attached to the plastic, outside film 12.

To interrupt and divide the adhesive material 25 into segments 29 a first portion of a nonadhesive flexible sheet material 26 having a multiplicity of openings 28 is attached preferably to the entire adhesive surface 25 of the second extendable portion 24 of the tape 21. In the embodiment being described there is no adhesive on the second portion 24 adjacent the edge of the diaper; the first portion of the open sheet material is attached to the adhesive material on the remaining segment of the second portion 24.

A second portion 27 of the open sheet material is attached to the opposite surface of the diaper from which the first portion 22 of the tape is attached, in this instance, the inside surface 14. As can be seen in FIG. 2, the attachment of the second portion 27 of the open sheet material thereby effectuates a "Y" shaped structure: one leg of the "Y" is the first portion 22 of the tape (on the outside surface 12); the other leg of the "Y" is the second portion 27 of the open sheet material (on the inside surface 14); and the stem of the "Y" is the first portion 24 of the tape. This arrangement distributes the forces while the tape is being fastened and when the tape is in use, as will hereinafter be described.

While the second portion 27 of the open sheet material may be fastened by any convenient means to its respective surface of the diaper, one functional technique is to sandwich it between the diaper surface and a release sheet 15. Adhesive on one surface of the release sheet 15 secures the second portion 27 to the diaper surface through the openings in the sheet material; the top surface 16 is adhesively releasable and protects the adhesive on the second, extendable portion 24 of the tape. Second portion 24 of tape is folded over the release sheet 15 in superimposed relationship before the diaper is used. Easy separation of the second, extendable portion 24 from the release sheet 15 places the tape tab in position for fastening of the diaper.

In the open sheet material the multiplicity of openings 28 is formed by filaments 30 or portions of the material which border the openings. These filaments 30 may be strands of material in a structure of fabric woven in a very loose weave or scrim as to produce large openings or spaces 28 between adjacent strands. These filaments may be the land portions of a nonwoven fabric produced so as to have a flat, planar construction with a multiplicity of discontinuous openings or holes located therein.

It has been found preferable to use a sheet material 26 in which the filaments 30 are integral in nature at the junctures 31 where they intersect; i.e., the filaments 30 merge together in the same plane rather than being characterized by overlapping, or criss-crossing as might be found in a woven fabric. The more planar construction of the sheet material provides a more consistent, uniform contact between sheet material 26 and the adhesive layer 25 on the tape; it also lies evenly against or in the adhesive layer so that the adhesive areas through the openings 28 are interrupted and divided into distinct segments 29.

The openings 28 in the sheet material 26 define the size of the distinct adhesive segments 29 on the second portion 24. It is the explicit purpose of the smaller, reduced adhesive segments 29 to reduce the area over which the second portion is to be peeled from the plastic film. Specifically, it has been mentioned above that when a standard sized adhesive tape tab is peeled from a thin plastic film tearing readily occurs. One of the causes of this tearing is that over the total area of the tape tab the peel strength between tape tab and plastic film exceeds the tearing strength of the thin plastic film.

To rectify that problem this new tape tab is divided into smaller segments of adhesive areas 29 as seen in the drawings. Each adhesive segment 29 is separated or interrupted from adjacent adhesive segments by nonadhesive areas, in this case, the filaments 30 of the sheet material 26. When peeling the second portion 24 of the tape 21 from the plastic film 12 with the adhesive segments 29 thereon, an interrupted peeling action occurs.

The effect of the interrupted peeling is that peeling stresses which induce tearing are restricted to a much smaller area. In this respect, it has become possible to reduce the peeling strength between adhesive tape and plastic film below the tearing strength of the plastic film over that reduced area. Thus, the complete peeling action becomes a series of smaller or short peeling actions interrupted by the nonadhesive areas upon dividing the adhesive segments.

For thin plastic film, such as polyethylene having a thickness between 0.00075 and 0.0015 inches (0.0019 and 0.0038 cm.), typical tearing strengths range between approximately 1.5 and 3.0 lb/in$^2$ (105 and 210 g./cm$^2$). These values are determined by measuring the amount of force required to tear a unit area of the film when the force is applied to the film, e.g., pulling forces on the film at a 90° angle to the film. Similarly, the peel strength between an adhesive tape and the film can be determined by measuring the amount of force applied, for instance, at a 90° angle, to the tape over a given area which is required to peel the tape from the film. Of course, if the film tears, the peel strength between tape and film has exceeded the tearing strength of the film. It has been determined that when using a plastic netting sheet material 26 as the nonadhesive areas on the second portion 24 as seen in the drawings individual adhesive segments 29 having areas less than 0.250 in.$^2$(1.61 cm.$^2$) produce a peel strength of tape to film less than the tearing strength of the film. The thickness of the plastic netting employed to provide these results lies between 0.002 and 0.012 inches (0.0051 and 0.0305 cm.).

When using the concept of this invention the reduction of the peel strength of tape to film to a safe level generally has a somewhat diminished effect on the holding strength of the tape to the diaper, with particular reference to individual adhesive segments. However, when a plurality of smaller adhesive segments is accumulated as a whole on the adhesive tape surface, there is sufficient holding strength and shear strength to maintain satisfactory performance of the adhesive tape during contemplated use. As seen in FIG. 2, the openings 28 in the netting provide a plurality of adhesive segments 29; these segments 29, while having reduced peel strength on an individual basis, provide more than adequate holding strength of the tape to diaper on a combined basis.

The shapes of the adhesive segments 29 which are defined by the nonadhesive filaments in the tape 21 may take any geometric configuration. For instance, the adhesive segments may conveniently be circles, squares, rectangles, triangles, ellipses or any other shape, provided that the area confined by the outline of those shapes can be controlled to provide the proper relationship between peel strength and tearing strength as described above.

To divide the adhesive portion 25 of the second portion 24 of the tape into smaller segments each adhesive segment is interrupted or separated from adjacent adhesive segments by nonadhesive areas. These nonadhesive areas break up the stress area due to peeling forces and introduce sufficient discontinuity in the peeling action to confine the peeling stresses to the areas of the smaller adhesive segments. The nonadhesive areas may be strips of nonadhesive material on top of the adhesive surface, such as plastic filaments, to provide interruptions and divisions in the adhesive surface, or various other flexible, nonadhesive open sheet materials.

It has been found desirable and very practical to produce a plurality of smaller adhesive segments by using a nonadhesive, open-mesh sheet material or netting placed in the adhesive material on the extendable, second portion of the tape. Textile materials such as loosely woven scrim fabrics, nonwoven fabrics with a plurality of open areas, and plastic netting material with intersecting or overlapping filaments produce excellent results when used in this invention. Preferably, an open or reticulated plastic netting with integrally intersecting filament junctures is the most desirable and functional material to be used in conjunction with the adhesive tape. Reticulated plastic nettings described in U.S. Pat. No. 3,666,609 are good examples of the type of plastic sheet material which is advantageously used in the invention. These plastic products are flat, sheet-like synthetic polymers with a plurality of openings formed by filaments which are integrally joined at the intersections. The synthetic polymers preferably used to form the open sheet in this invention are the polyolefins, more particularly, polypropylene and polyethylene.

As another aspect of the present invention there is shown in FIG. 2 a segment 33 of the open sheet material which extends beyond the furthest edge of the tape 21. The segment 33 of the sheet 26 overhanging the furthest or distal edge of the second portion 24 of the tape is free, unsecured and is not covered by any adhesive. It is the purpose of this over-hanging, extending material to act as a pull-tab to aid in the peeling of the tape from the diaper after a closure has been made.

A fastened disposable diaper 10 is shown in FIG. 3, the diaper secured with the improved adhesive tape tabs. The second portion of the tape 24 which includes the open sheet material 26 is pressed against the plastic film 12 of the diaper so that the adhesive segments exposed by the openings of the material 26 make contact with the plastic film 12 thereby effectuating a closure. The over-hanging portion or segment 33 of the sheet material 26 is free and unsecured, and acts as a convenient pull-tab when the diaper need be opened. Of course, when employing the over-hang feature it is desirable to use a sheet material, such as a net, with a tensile strength greater than peel strength between tape and diaper; this assures that the overhanging segment will not tear off when peeling.

The effect of the peeling action aided by the overhanging segment of open-mesh sheet material, and the distribution of fastening forces to both sides of the diaper are clearly shown in FIG. 4. In the fastened position two corners of the diaper 10 overlap and are secured together by the adhesively coated second portion 24 of the tape 21 making contact with a part of the outside plastic film 12. Movement of the wearer often causes stress forces generally in the shear directions of the fastened components. Thus, the force perceived by the second portion 24 of the tape is indicated by $F_1$. This force is transmitted to the two legs of the "Y" as described above; force, $F_2$ is seen on the second portion 27 of the plastic net, on the inside surface 14 of the diaper; force, $F_3$ is seen on the first portion 22 of the tape, on the outside surface 12 of the diaper. By distributing force $F_1$ to both surfaces of the diaper, forces $F_2$ and $F_3$, the stress, especially on the plastic film 12, is significantly reduced which also decreases the frequency of film tearing induced when the diaper is fastened, or at other times.

When a closed diaper 10 using the preferred embodiment of the improved tape tab of this invention needs inspection or adjustment or whatever reason for opening, the first step is to conveniently take hold of the overhanging segment 33 of sheet material 16. By pulling the overhanging segment 33 back in the direction over the tape 21 (as shown by the arrow in FIG. 4), the second portion 24 of the tape can be readily separated from the backing sheet 12 of the diaper. In this embodiment the overhanging or extending open sheet material 33 on the adhesive portion tape 24 assists in peeling the second portion of tape evenly and cleanly over the stress area. Peeling forces transmitted along the tape are also distributed to both surfaces of the diaper to reduce stress levels on those surfaces.

Furthermore, additional closures of the diaper can be made in the same fashion the original closure was made. Once the tape is peeled from the previously fastened position on the surface 12 of the diaper, the outside plastic film 12 is not torn or ripped, and sufficient adhesive remains on the adhesive segments to be used again. The extendable, second portion of the tape can be fastened to the diaper in the same location as previous closures were made, or in a different location if a different or neater fit is required of the diaper on re-use. The tape is re-used in the same fashion an original closure is made; i.e., the tape is pressed against the fastening surface so that the adhesive portions 29 of the second portion 24 of the tape exposed by the openings in the sheet material 26 make adhesive contact on the diaper. These additional closures are strong and sufficiently adequate to hold the diaper in a fixed position during use. The convenience of the tape tab of this invention allows many openings and refastenings during the normal service of the diaper.

When the nonadhesive areas located on the extendable portion of the adhesive tape tab are raised or protrude above the adhesive material the new tab may be stored or packaged before use without an additional protective release sheet. For instance, depending upon the fold of the diaper the extendable portion of the tape may rest, adhesive surface down, against the inside surface or facing of the diaper. By allowing the nonadhesive filaments to rest against the inside surface of the diaper there is no need to cover the adhesive segments of the tab with a protective release sheet. When the diaper is ready for use there is nothing, such as a release sheet, to peel or from which to peel in order to use the tape tab. The user merely lifts the tab away from its resting position and places the diaper around the wearer.

While it is feasible to utilize some embodiments of the adhesive tape tab of this invention without protective release sheets, those sheets and other means may be desirably used when convenient or suitable in order to protect the adhesive surface of the extendable portion of the tape before use.

Another advantage of the new tape tab of this invention is in the final opening of the diaper, when the diaper is ready to be discarded. The new tape tab allows the diaper to be opened cleanly, with no untidy tearing, while sufficient adhesive remains on the tape for one last function. After the diaper is removed from the wearer, it may be folded or rolled and then sealed closed with the tape tabs so that the contents are contained securely within in order to be discarded.

This invention is further illustrated by the following Examples which should not, however, be construed as fully delineating the scope of this discovery.

EXAMPLE I

An adhesive tape tab for use on disposable diapers is formed by attaching a first portion of a tape to the outside surface of the diaper which is made of polyethylene film, 0.001 inch (0.0025 cm.) thick. The tearing strength of the polyethylene film is approximately 2.0 lb/in$^2$ (140 g./cm$^2$). A first portion of a flat, open planar sheet of plastic netting material with integrally intersecting intersections is attached to an adhesively treated surface of tape. The plastic sheet material is made of polypropylene and the first portion thereof is attached to the portion of the tape which is extendable beyond the edge of the diaper; however, on the extendable portion of tape there is no adhesive for about ⅛ inch (0.318 cm.) in the portion immediately adjacent the edge of the diaper. The plastic sheet material also has a segment extending beyond the distal or furthest edge of the tape. A second portion of plastic netting is attached to the inside surface of the diaper by a release sheet which has an adhesively releasable top surface. The plastic sheet contains openings in the form of rectangles, each rectangle having an open area of approximately 0.041 square inches (0.264 sq. cm.). The thickness of the plastic sheet is approximately 0.005 inches (0.0127 cm.). The openings of the plastic sheet material form adhesive segments in the extendable portion of the tape. When this tape tab fastens the diaper during use and opening of the tape is required the extendable portion of tape is readily peeled from the polyethylene film, since the peel strength between the tape and the film over the individual adhesive segments is less than the tearing strength of the film over the same individual adhesive segments. Furthermore, any fastening or peeling forces transmitted along the second portion of the tape are distributed to both surfaces of the diaper.

EXAMPLE II

The open plastic netting of Example I is attached to the tape and to the inside surface of the diaper such that the longitudinal filaments of the sheet form an angle of 45° with the longitudinal direction of the tape. The openings in the length and width-wise directions of the sheet are the same as in Example I.

The tape tab with this open plastic sheet makes an excellent closure on the diaper, distributing fastening forces to both surfaces of the diaper during use, and is readily separated when diaper checking, repositioning or the like is required.

Thus, it is apparent that there has been provided, in accordance with this invention, an improved, reusable, force distributing adhesive tape tab for use on disposable diapers that fully satisfies the aims, advantages and aspects set forth above. While the invention has been described in conjunction with specific embodiments thereof, it is evident that many alternatives, modifications and variations will be apparent to those skilled in the art in view of the foregoing description. Accordingly, the plenary invention is intended to embrace all such alternatives, modifications and variations as fall within the broadest scope and spirit of the described invention.

What is claimed is:

1. In a disposable diaper of the type having an inside surface and an outside surface, an improved adhesive tape tab comprising: a tape having a first portion attached to one surface of the diaper and having a second, extendable portion for attachment to another part of the diaper; adhesive material on one surface of the second portion of said tape; a flexible, open-mesh sheet material having a first portion fixedly attached to the adhesive surface of the second portion of said tape, and having a second portion fixedly attached to the surface of the diaper opposite from the surface which said first portion of said tape is attached, whereby during use fastening forces transmitted by the second, extendable portion of said tape are distributed to the inside and outside surfaces of said diaper through said tape first portion and said open-mesh second portion.

2. An improved adhesive tape tab as defined in claim 1 wherein the flexible, open-mesh sheet material is plastic.

3. An improved adhesive tape tab as defined in claim 2 wherein the plastic material is flat and sheet-like with a multiplicity of openings formed by filaments which are integrally joined at the intersections.

4. An improved adhesive tape tab as defined in claim 1 wherein the first portion of said open-mesh sheet material is attached to substantially the entire second, extendable portion of said tape.

5. An improved adhesive tape tab as defined in claim 1 wherein the first portion of said open-mesh sheet material extends beyond the distal edge of said second, extendable portion of said tape, whereby said extending portion of sheet material acts as a pull-tab for peeling purposes.

6. An improved adhesive tape tab as defined in claim 1 wherein the second, extendable portion of said tape is free from adhesive on said one surface thereof in an area immediately adjacent the edge of said diaper, and the first portion of said open-mesh sheet material is attached to said adhesive material on the remaining segment of the second, extendable portion of said tape.

7. An improved adhesive tape tab as defined in claim 1 wherein the second portion of said open-mesh sheet material is attached to said surface by a release sheet, the top surface of said release sheet being adhesively releasable to protect the adhesive on the second, extendable portion of said tape which lies in an overlying relationship on said release sheet before use thereof.

8. An improved tape tab as defined in claim 1 wherein the outside surface of the diaper is a thin plastic film and the second, extendable portion of said tape is attachable thereto, the first portion of said open-mesh sheet material dividing said adhesive material into segments, each of said adhesive segments having an area so that the peel strength between said second portion of tape and said film over said segmented area is less than the tearing strength of said film over the same segmented area.

* * * * *

UNITED STATES PATENT AND TRADEMARK OFFICE
CERTIFICATE OF CORRECTION

PATENT NO. : 4,059,125

DATED : November 15, 1977

INVENTOR(S) : Irving S. Ness

It is certified that error appears in the above-identified patent and that said Letters Patent are hereby corrected as shown below:

At Column 4, Line 2, "tap" should be -- tape --.
At Column 8, Line 3, "16" should be -- 26 --.

Signed and Sealed this

Fourteenth Day of November 1978

[SEAL]

Attest:

RUTH C. MASON
Attesting Officer

DONALD W. BANNER
Commissioner of Patents and Trademarks